United States Patent
Lipp

(10) Patent No.: US 7,607,435 B2
(45) Date of Patent: Oct. 27, 2009

(54) GAS OR LIQUID FLOW SENSOR

(75) Inventor: Brian A. Lipp, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 223 days.

(21) Appl. No.: 10/763,040

(22) Filed: Jan. 21, 2004

(65) Prior Publication Data

US 2005/0155602 A1    Jul. 21, 2005

(51) Int. Cl.
*A61M 16/00* (2006.01)
*A61M 15/00* (2006.01)

(52) U.S. Cl. .............................. 128/203.13; 128/203.12

(58) Field of Classification Search ............ 128/200.14, 128/200.11, 204.23, 204.18, 204.21, 200.21; 600/529, 586, 532, 538–542; 73/861; 422/83, 422/84; 604/58

See application file for complete search history.

(56) References Cited

U.S. PATENT DOCUMENTS

| | | | | |
|---|---|---|---|---|
| 4,676,237 A | * | 6/1987 | Wood et al. ............. | 128/203.17 |
| 4,729,244 A | | 3/1988 | Furuse ..................... | 73/861.74 |
| 5,086,785 A | | 2/1992 | Gentile et al. ............... | 128/782 |
| 5,157,372 A | | 10/1992 | Langford .................... | 338/211 |
| 5,161,541 A | * | 11/1992 | Bowman et al. ............ | 600/537 |
| 5,311,875 A | * | 5/1994 | Stasz .......................... | 600/537 |
| 5,392,768 A | | 2/1995 | Johansson et al. ........ | 128/200.14 |
| 5,394,866 A | * | 3/1995 | Ritson et al. ........... | 128/200.14 |
| 5,404,871 A | * | 4/1995 | Goodman et al. ...... | 128/200.14 |
| 5,469,750 A | | 11/1995 | Lloyd et al. .............. | 73/861.61 |
| 5,487,378 A | | 1/1996 | Robertson et al. ...... | 128/200.16 |
| 5,497,764 A | | 3/1996 | Ritson et al. ........... | 128/200.14 |

(Continued)

FOREIGN PATENT DOCUMENTS

WO    WO 92/07600    5/1992

(Continued)

OTHER PUBLICATIONS

U.S. Provisional Patent Application, entitled "Inhaler Device" by David E. Adams, pp. 1-4 (copy attached). Drawings unavailable to applicant.

(Continued)

*Primary Examiner*—Justine R Yu
*Assistant Examiner*—Annette F Dixon
(74) *Attorney, Agent, or Firm*—Patricia A. Coburn

(57) ABSTRACT

An air flow sensor comprises a flexible resistive element permanently affixed to a flexible substrate. The air flow sensor is positioned in an inlet for airway to be monitored such that the sensor covers the inlet at all times other than during inhalation. When a vacuum is applied to the airway, a resulting drop in air pressure within the airway causes air to flow through the inlet and airway, causing the sensor's substrate to flex. Flexure of the substrate also causes a resistive element to flex, resulting in a change in the electrical resistance of the resistive element, such as an increase in resistance. Flexure of the sensor is enhanced by flexible leads, which serve as a hinge point. An air shield may be positioned around the periphery of the air flow sensor to channel and restrict the movement of air flowing through the air inlet, thereby enhancing movement of the sensor.

19 Claims, 6 Drawing Sheets

U.S. PATENT DOCUMENTS

| | | | |
|---|---|---|---|
| 5,509,404 A | 4/1996 | Lloyd et al. | 128/200.14 |
| 5,522,378 A * | 6/1996 | Ritson et al. | 128/200.14 |
| 5,542,410 A | 8/1996 | Goodman et al. | 128/200.14 |
| 5,558,099 A * | 9/1996 | Bowman et al. | 600/538 |
| 5,577,497 A | 11/1996 | Mecikalski et al. | 128/203.15 |
| 5,655,516 A | 8/1997 | Goodman et al. | 128/200.14 |
| 5,655,523 A | 8/1997 | Hodson et al. | 128/315 |
| 5,694,920 A | 12/1997 | Abrams et al. | 128/200.16 |
| 5,755,218 A | 5/1998 | Johansson et al. | 128/200.14 |
| 5,813,397 A * | 9/1998 | Goodman et al. | 128/200.14 |
| 5,823,178 A | 10/1998 | Lloyd et al. | 128/200.14 |
| 5,826,570 A | 10/1998 | Goodman et al. | 128/200.14 |
| 5,832,592 A | 11/1998 | Bowman et al. | 29/612 |
| 5,855,564 A | 1/1999 | Ruskewicz | 604/62 |
| 5,894,841 A | 4/1999 | Voges | 128/203.12 |
| 5,950,619 A * | 9/1999 | van der Linden et al. | 128/200.16 |
| 6,116,238 A | 9/2000 | Jackson et al. | 128/203.15 |
| 6,152,130 A | 11/2000 | Abrams et al. | 128/204.21 |
| 6,158,431 A | 12/2000 | Poole | 128/203.12 |
| 6,260,549 B1 | 7/2001 | Sosiak | 128/200.23 |
| 6,318,361 B1 | 11/2001 | Sosiak | 128/200.23 |
| 6,397,838 B1 | 6/2002 | Zimlich, Jr. et al. | 128/200.14 |
| 2002/0092519 A1* | 7/2002 | Davis | 128/200.14 |
| 2002/0104530 A1* | 8/2002 | Ivri et al. | 128/200.16 |
| 2002/0174724 A1 | 11/2002 | Benzel | 73/762 |
| 2004/0055595 A1* | 3/2004 | Noymer et al. | 128/200.14 |
| 2004/0081587 A1* | 4/2004 | Melker et al. | 422/84 |

FOREIGN PATENT DOCUMENTS

| | | |
|---|---|---|
| WO | WO 94/16757 | 8/1994 |
| WO | WO 94/19042 | 9/1994 |
| WO | WO 97/05824 | 2/1997 |
| WO | WO 02/068031 | 9/2002 |

OTHER PUBLICATIONS

EP Supplementary European Search Report for EP04812741 dated Sep. 20, 2007.

* cited by examiner

Fig. 5

GAS OR LIQUID FLOW SENSOR

FIELD

The present invention relates generally to a sensor for detecting air flow. In particular, the present invention relates to a sensor adapted to function as an air flow detector for breath-actuated devices.

BACKGROUND

The ability to detect the presence of air flow is a key element of many systems and devices. For example, most combustion systems require a means for sensing air flow to ensure that sufficient air is being provided for proper combustion. Likewise, many industrial and manufacturing processes depend on sensors to monitor air movement, such as baking and curing processes that utilize air flow to evenly distribute heated air. Still another use for air flow sensors is monitoring exhausts of various equipment to ensure that the exhaust system is functioning properly.

Air flow sensing is also an essential element of numerous medical applications. For example, air flow sensors may be used in conjunction with control electronics to form a breath-actuated electrical interface which enables paraplegics to control a wide variety of electrical, electronic and electromechanical devices.

Air flow sensors are particularly desirable for use as inhalation sensors in association with pulmonary medication delivery devices. Delivery of medication via inhalation offers several advantages over other methods of medication delivery. For example, inhalation is less invasive to the patient than intravenous or intramuscular injection, which requires piercing of the patient's skin. Such injections cause discomfort for the patient and may also increase the risk of infection. Delivery of medications orally also suffers from various drawbacks, such as low absorption rate, relatively low absorption level, and potential incompatibility with many patients, particularly those with digestive disorders. Similarly, transdermal patches have a relatively low absorption rate and low absorption level. In contrast, inhalation delivery is non-invasive, reducing patient discomfort and the risk of infection while providing a high absorption rate and a high absorption level. In addition, medications may be delivered via inhalation in many cases when the patient is unable to orally ingest medications.

Several obstacles must be overcome to effectively deliver medications via inhalation. Firstly, the medication must typically be stored in a solid, liquid or powder form and then aerosolized. The aerosolized medicine must then be mixed with breathing air at an appropriate concentration and air pressure to facilitate efficient delivery, yet not interfere with the patient's breathing. In addition, the mixing of the medication and the air must be controlled such that the patient is provided a known dosage. Finally, the air-medication mixture must be delivered to the patient with a minimum of loss, such as by leakage, since lost medication results in wastage and reduced accuracy in dosage measurement.

Air flow sensors, also known as "breathing sensors" and "inhalation sensors," are frequently used in conjunction with inhalation devices to synchronize the release of medication with inhalation. Synchronized release is desirable to ensure delivery of the medicine and minimize waste, since the medication is delivered only during inspiration.

A number of devices have been developed to measure air flow, with some success. A well-known air flow sensing device is a vane-actuated or "sail" switch, such as used with the inhaler disclosed by Mecikalski et al. in U.S. Pat. No. 5,577,497. An electrical switch is coupled to an actuator that is adapted to be displaced by air flow. The actuator is typically lightweight and includes a surface area arranged to at least partially block an airway such that the actuator is moved due to pressure exerted against it by flowing air, resulting in actuation of the switch. Although sail switches are in common use, they suffer from a number of shortcomings. For example, sail switches are difficult and cumbersome to set for actuation at a particular desired airflow level. This is due to the criticality of the actuator's position in the airway for proper operation, coupled with the inherent mechanical variations present in airways, actuators and electrical switches. In addition, variations in air flow can cause erratic actuation of the switch. Further, sail switches are susceptible to the vibration and shock typically encountered during normal handling, which can cause unintended actuation or undesired changes to the switch's actuation setpoint.

Another well-known air flow sensor is a pressure transducer, such as used with the medication dispenser disclosed by Johansson et al. in U.S. Pat. No. 5,392,768. The pressure transducer detects air flow by measuring pressure changes with resistive or piezoresistive strain gauges that are implanted on a membrane or diaphragm. The membrane or diaphragm is displaced by air flow, and the displacement is indicated by a change in the electrical value of the strain gauge. Although pressure transducers overcome many of the mechanical limitations of sail switches, they also have a number of limitations. In particular, pressure transducers suffer from thermal and long-term drift, reducing the accuracy of the pressure switch and necessitating the use of various compensation measures, such as expensive narrow-tolerance electronic components and offset compensation circuitry or software programs. In addition, the output signal of pressure transducers may vary with the orientation of the transducer, further reducing the accuracy and/or repeatability of the air flow sensor's actuation setpoint.

Use of a hot-wire anemometer or mass flow sensor to measure air flow is also common in the art, such as used with an inhaler disclosed by Robertson et al. in U.S. Pat. No. 5,487,378. A resistive wire is electrically heated to a predetermined temperature. As air flowing around the heated wire cools it, the electrical current flowing through the wire is increased to return it to the predetermined temperature. Since the amount of air moving around the wire is directly related to the amount of cooling experienced by the heated wire, a feedback arrangement may be established whereby the current flowing through the wire is measured to sense whether or not air is flowing. However, the cooling effect of the air can vary, depending on the velocity, temperature, humidity and density of the air, reducing the accuracy and/or repeatability of the air flow sensor's actuation setpoint under varying environmental conditions. In addition, relatively complex electronic circuitry is required to convert the electrical current flowing through the wire to a logical signal that indicates whether or not air is flowing.

The prior art also includes angular displacement sensors and flexible potentiometers (collectively termed "flexible sensors" herein) that utilize a resistive ink screened or deposited onto a flexible substrate. The resistance of the resistive ink changes when the substrate is flexed, providing an electrical indication of the displacement of the substrate. Examples of flexible sensors are disclosed by Langford in U.S. Pat. No. 5,157,372 and by Gentile et al. in U.S. Pat. No. 5,086,785. However, prior art flexible sensors suffer from a relatively high cost due to the process steps and materials required to place a low-resistance conductor over the resistive ink to lower the nominal resistance of the flexible sensor. The low-resistance conductor also adds to the thickness of the flexible sensor, reducing its flexibility and thus limiting the flexible sensor's ability to detect relatively low levels of air flow.

Other air flow sensing devices are available in the art, such as thermally sensitive resistors, thermally sensitive crystals and piezoelectric actuators. However, these devices likewise suffer from at least some of the mechanical, electrical and environmental limitations of the aforementioned devices.

Several of the aforementioned air flow sensors have been used in conjunction with breath-actuated pulmonary medicine delivery devices, with some success. However, the drawbacks associated with these sensors can result in greater manufacturing expense, reduced accuracy and/or repeatability under varying environmental conditions, and a need for careful handling.

There is a need for an air flow sensor capable of operating accurately and repeatably under varying environmental conditions. There is a further need for an air flow sensor that is robust and capable of withstanding normal handling and orientation without degradation in performance. There is a still further need for an air flow sensor that does not require complex electronic circuitry. There is a particular need for an air flow sensor capable of reliably and repeatably sensing air flow resulting from a patient's inhalation to trigger a handheld drug delivery device to deliver a known dosage of medication.

SUMMARY

The present invention overcomes the aforementioned limitations of present air flow sensors. Specifically, according to an embodiment of the present invention, an air flow sensor comprises a flexible transducer affixed to a flexible substrate. The air flow sensor is positioned proximate an inlet for an airway such that the sensor covers the inlet unless air is flowing into the inlet. When reduced air pressure is present in the airway, the pressure differential between the ambient atmosphere and the airway causes air to flow into the airway via the inlet. The flowing air impinges the sensor, displacing or "flexing" the substrate. Flexure of the substrate causes the transducer to flex, resulting in a change in the electrical value of the transducer. Flexure of the sensor is enhanced by flexible leads, which extend hingedly between an inlet-covering portion and a mounting portion. An air shield may be positioned around the periphery of the sensor to channel and restrict the movement of air flowing through the air inlet, thereby enhancing movement of the sensor.

The air flow sensor is ideal for use in a pulmonary medication delivery apparatus, particularly hand-held inhalation drug delivery devices, since the sensor is mechanically robust and is both electrically and environmentally stable. Since medication is dispensed to the patient only during inhalation, the patient is assured of receiving a proper dose with minimal waste. In addition, the inhalation sensor provides an automatic means of controlling the delivery of medication, making the present invention usable by a patient with minimal medical supervision.

An object of the invention is a sensor for detecting movement of air. The sensor comprises a flexible substrate. A flexible transducer is affixed to the substrate. The transducer comprises a first end and a second end. A first electrical contact is in electrical communication with the first end of the transducer, and a second electrical contact is in electrical communication with the second end of the transducer. A protective covering is placed over at least a portion of at least one of the transducer, first electrical contact and second electrical contact. The substrate is displaced when positioned in a stream of moving air, the displacement of the substrate causing flexure of the transducer and changing the electrical value of the transducer.

Another object of the present invention is a sensor for detecting inhalation. The sensor comprises a flexible substrate. A flexible transducer is affixed to the substrate, the transducer comprising a first end and a second end. A first electrical contact is in electrical communication with the first end of the transducer, and a second electrical contact is in electrical communication with the second end of the transducer. A protective covering is placed over at least a portion of at least one of the transducer, first electrical contact and second electrical contact. The substrate is displaced when positioned in a stream of moving air caused by inhalation, the displacement of the substrate causing flexure of the transducer and changing the electrical value of the transducer.

Still another object of the invention is a sensor for detecting movement of air. The sensor comprises a flexible substrate. At least one flexible lead is integral to the substrate. A flexible resistive ink transducer affixed to the flexible lead such that the transducer comprises a first end and a second end. A first electrical contact is in electrical communication with the first end of the transducer. A second electrical contact is in electrical communication with the second end of the transducer. A protective covering is placed over at least a portion of at least one of the transducer, first electrical contact and second electrical contact. The substrate is displaced when positioned in a stream of moving air. The displacement of the substrate causes flexure of the transducer and changes the electrical value of the transducer.

Yet another object of the present invention is a device for delivering medication. The device comprises an air inlet. An airway is in pneumatic communication with the air inlet. A sensor for detecting movement of air is positioned in the airway proximate the air inlet such that the sensor is effective to selectively close the air inlet. The device further comprises a reservoir for containing medication. A pump/valve is in pneumatic communication with the reservoir. An aerosolation spray means is in pneumatic communication with the pump/valve. A mouthpiece is in pneumatic communication with the airway and the aerosolation spray means. An electrical power supply provides electrical power for the device. A controller portion is in electrical communication with the power supply, sensor, pump/valve and aerosolation means. In operation, air flowing into the airway from the inlet displaces the sensor, changing the electrical value of the sensor. The controller portion detects the change in electrical value of the sensor and actuates the pump/valve. The pump/valve urges medication to flow from the reservoir to the aerosolation means. The aerosolation means aerosolizes the medication. The air flowing into the airway is combined with the aerosolized medication in the mouthpiece for delivery to a patient.

Still another object of the present invention is an alternate device for delivering medication. The device comprises an air inlet. An airway is in pneumatic communication with the air inlet. A sensor for detecting movement of air is positioned in the airway proximate the air inlet such that the sensor is effective to selectively close the air inlet. The device further comprises a reservoir for containing medication. A pump/valve is in pneumatic communication with the reservoir. An electrohydrodynamic aerosolation spray means is in pneumatic communication with the pump/valve. A mouthpiece is in pneumatic communication with the airway and the electrohydrodynamic aerosolation spray means. An electrical power supply provides electrical power for the device. A controller portion is in electrical communication with the power supply, sensor, pump/valve and electrohydrodynamic aerosolation means. In operation, air flowing into the airway from the inlet displaces the sensor, changing the electrical value of the sensor. The controller portion detects the change in electrical value of the sensor and actuates the pump/valve. The pump/valve urges medication to flow from the reservoir to the electrohydrodynamic aerosolation means. The electrohydrodynamic aerosolation means aerosolizes the medication. The air flowing into the airway is combined with the aerosolized medication in the mouthpiece for delivery to a patient.

BRIEF DESCRIPTION OF THE DRAWINGS

Further features of the inventive embodiments of the present invention will become apparent to those skilled in the art to which the embodiments relate from reading the specification and claims with reference to the accompanying drawings, in which:

FIG. 5 is a functional block diagram of a typical breath-actuated pulmonary medication delivery apparatus according to an embodiment of the present invention;

DETAILED DESCRIPTION

Figure 1A:
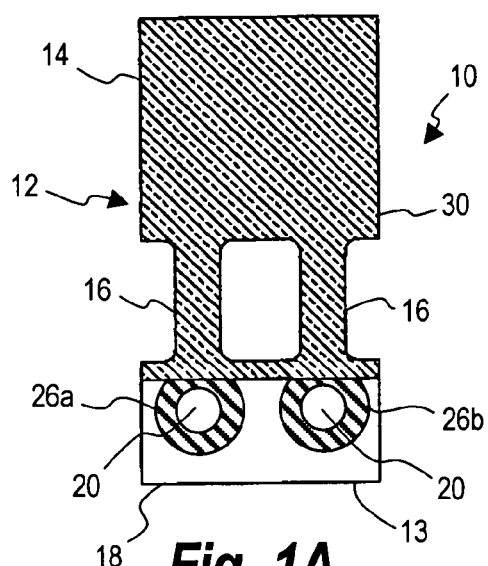
FIG. 1A is a top plan view of an air flow sensor according to an embodiment of the present invention.

Throughout this specification the terms "drug," "medication" and "medicine" are used interchangeably to describe any appropriate respirable, therapeutically active material or diagnostic agent. In the figures, like parts have been given like reference numerals.

Figure 1B:
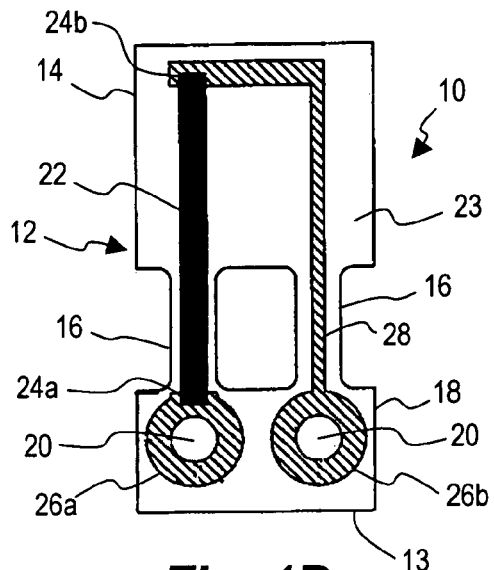
FIG. 1B is a top plan view of the air flow sensor of FIG. 1A with a protective covering removed to expose the components of the sensor.
Figure 1C:
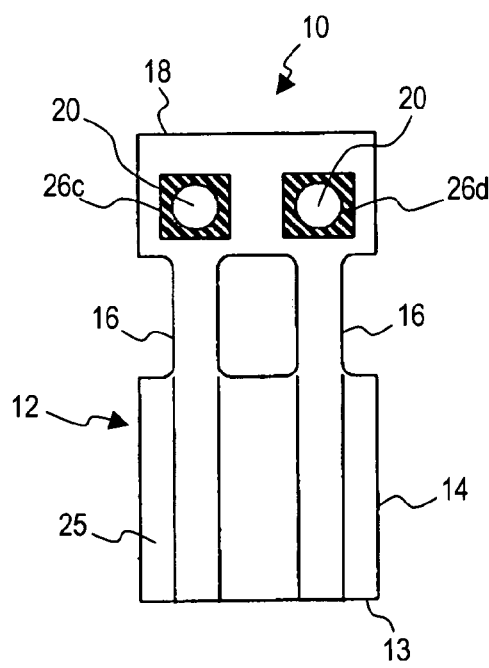
FIG. 1C is a bottom plan view of the air flow sensor of FIG. 1A.

The general arrangement of an air flow sensor 10 according to an embodiment of the present invention is depicted in FIGS. 1A-1C. Sensor 10 comprises a body 12 having an air inlet-covering portion 14, flexible leads 16, a mounting portion 18, and a transducer 22.

Body 12 comprises a flexible substrate 13 that is preferably made of a non-conductive material such as, but not limited to, TEFLON®, KAPTON® or other polyimides, MYLAR®, and plastics. Flexible substrate 13 preferably does not exhibit a "memory" effect when bent, and thus returns to its original shape and orientation when the bending force is removed. Body 12 is shown in FIGS. 1A-1C as being generally rectangular in shape, but may be made in any shape desired to accommodate particular airways, air inlets and housings, to facilitate manufacture, or to increase displacement of the sensor in flowing air. Example body 12 embodiments include, but are not limited to, circular, elliptical, polygonal, triangular, trapezoidal, "horseshoe," "U," and parallelogram shapes.

Air inlet-covering portion 14 is adapted to be positioned proximate an air inlet 38 (see FIGS. 2A-2B) and effectively block the inlet when air is not flowing. Inlet-covering portion 14 is depicted in FIGS. 1A-1C as being generally rectangular in shape, but may be made in any shape desired to accommodate particular airways, air inlets and housings, or to facilitate manufacture. Example inlet-covering portion 14 embodiments include, but are not limited to, circular, elliptical, polygonal, triangular, trapezoidal, "horseshoe," "U," and parallelogram shapes. Inlet-covering portion 14 is preferably shaped to maximize deflection of sensor 10 for a given volume of air flow. Maximized deflection of sensor 10 is desirable to maximize flexure of transducer 22, as discussed in detail below.

At least one flexible lead 16 hingedly connects inlet-covering portion 14 to mounting portion 18. Flexible leads 16 are adapted to allow inlet-covering portion 14 to flex easily when impinged upon by flowing air. Flexible leads 16 may be any shape or length desired, so long as inlet-covering portion 14 effectively closes an air inlet when no air is flowing and flexes when air is flowing. Flexible leads 16 are preferred to increase the displacement of inlet-covering portion 14 by flowing air. In particular, flexible leads 16 are desirable to allow greater displacement of inlet-covering portion 14 for relatively low levels of air flow, such as air flows typical with respiration. If flexible leads 16 are not utilized, inlet-covering portion 14 is directly coupled to mounting portion 18.

Mounting portion 18 is adapted to be removably secured to a mounting point such that inlet-covering portion 14 is located proximate an air inlet. In the embodiment of the present invention shown in FIGS. 1A-1C, mounting portion 18 further comprises a pair of openings 20 through which conventional mounting means 34 (see FIGS. 2A-2B) may be fitted to secure the sensor 10.

Sensor 10 further comprises a flexible transducer 22 (hereinafter termed "flexible transducer" or "transducer") permanently affixed to a component side 23 of substrate 13, as best shown in FIG. 1B. Transducer 22 may be any conventional transducer capable of converting mechanical movement, stress or strain to an analogous electrical value. Example transducers include, but are not limited to, capacitive transducers, inductive transducers, resistive transducers and piezoelectric transducers.

In a preferred embodiment, transducer 22 is a resistive transducer comprised of a conventional resistive ink. Resistive inks typically comprise conductive carbon particles in a binder, and are printed or deposited onto flexible substrate 13. A variety of resistive ink formulations are available in the art from a number of suppliers, such as Amtech International of Branford, Conn.

The nominal resistance of the resistive ink is established by the composition and geometry of the resistive ink. The composition of the resistive ink is controlled by its formulation, which defines the amount and types of resistive materials, binders and carriers. Any resistive ink formulation having the desired electrical, physical and mechanical properties for a particular embodiment of sensor 10 may be selected. Example properties include resistivity, elasticity, amount of change in resistance for a predetermined amount of flexure of substrate 13, temperature coefficient of resistance, and operating temperature range. The nominal resistance "R" of transducer 22 is directly proportional to its length and inversely proportional to its cross-sectional area, i.e., the product of width and thickness of the resistive ink. The resistance of transducer 22 is given generally by Equation 1:

$$R = p \frac{\text{LENGTH}}{\text{CROSS-SECTIONAL AREA}} \quad \text{Equation 1}$$

where p is a resistivity constant of proportionality for a select formulation of the resistive ink.

Two physical reactions cause changes in the resistance of the resistive ink when substrate 13 is flexed. The first reaction occurs due to stretching and compressing forces exerted upon the ink. When flexible substrate 13 is bent such that the resistive ink is on the outer radius of the bend the ink stretches slightly, causing the distances between the carbon particles to increase. This causes a predictable increase in the electrical resistance of transducer 22. Conversely, when the resistive ink is on the inner radius of the bend the ink compresses slightly, causing the distances between particles to decrease, thus decreasing the resistance of transducer 22. The second physical reaction occurs when flexible substrate 13 is bent such that the resistive ink is on the outer radius of the bend. The bend causes "micro-cracks" to form in the ink in a direction generally transverse to the axis of the bend. As the bend increases, the width of these cracks increases, also contributing to an increase in the electrical resistance of transducer 22.

Resistive inks are preferred over resistive elastomers for transducer 22, as resistive inks do not exhibit the memory and resistive hysteresis common to resistive elastomers when bent. Thus, transducer 22 returns to the same general resistance value in its unbent position each time.

At least a portion of transducer 22 is preferably located in a region of maximum flexure of body 12, in order to maximize the amount of resistance change when inlet-covering portion 14 is deflected due to air flow. Locating transducer 22 in an area of maximum flexure also increases the transducer's sensitivity, since the change in resistance will be maximized for a given deflection of inlet-covering portion 14. A relatively high transducer 22 sensitivity is desirable for detecting air flow such as inhalation, since the volume of air flow may be relatively low, particularly for patients that have limited pulmonary capacity. In the embodiment shown in FIGS. 1A-1C, the region of maximum flexure of sensor 10 is the flexible leads 16 due to their hinging action when mounting portion 18 is secured or mounted to a non-moving structure and inlet-covering portion 14 is displaced by air flow.

A first end 24a of transducer 22 is electrically coupled to a first electrical contact 26a. An electrical conductor 28 extends between a second end 24b of transducer 22 and a second electrical contact 26b, electrically coupling the second end of the transducer to the second electrical contact. In an alternate embodiment, second end 24b of transducer 22 may be directly electrically coupled to second electrical contact 26b. Electrical contacts 26a, 26b and electrical conductor 28 may be made by screening or depositing a flexible conductive material, such as silver epoxy, onto substrate 13. Electrical contacts 26a, 26b and electrical conductor 28 may also be made by a conventional cladding and etching process such as well-known processes for fabricating electronic printed circuits. The present invention differs from prior art flexible sensors in that no low-resistance conductors are placed over transducer 22, since the resistance of the transducer is controlled by the formulation of the resistive ink and the geometry of the transducer, as previously detailed. Elimination of low-resistance conductors allows the production of a sensor 10 having a lower cost than prior transducers due to the reduction in material usage and fewer process steps. In addition, the elimination of the low-resistance conductors increases the flexibility of sensor 10 by reducing its thickness. The increased flexibility of sensor 10 allows for greater flexure of transducer 22 at low volumes of air flow, thereby further improving the sensitivity of the transducer.

As shown in FIG. 1A, a protective covering 30 may be placed over at least a portion of at least one of transducer 22, electrical conductor 28, and electrical contacts 26a, 26b to protect them from degradation and damage due to handling and exposure to the environment. Protective covering 30 may be made from any material compatible with body 12, transducer 22 and electrical conductor 28, but is preferably electrically non-conductive and flexible, such as TEFLON®, KAPTON® and other polyimides, MYLAR®, and plastics. In an alternate embodiment of the present invention, protective covering 30 may be a conventional conformal coating, such as silicone, acrylic, urethane, and epoxy. Protective covering 30 preferably does not exhibit a memory when bent, and returns to its original shape and orientation when the bending force is removed. Protective covering 30 may be shaped to terminate proximate electrical contacts 26a, 26b to at least partially expose the electrical contacts, as shown in FIG. 1A. In alternate embodiments of the present invention protective covering 30 may cover substantially all of component side 23 of body 12, with or without openings or voids in the protective covering for exposing at least a portion of electrical contacts 26a, 26b.

With reference to FIG. 1C and continued reference to FIGS. 1A-1B, a bottom plan view of sensor 10 is shown. A pair of electrical contacts 26c, 26d are affixed to a non-component side 25 of substrate 13 and generally aligned under contacts 26a, 26b respectively. In one embodiment of the present invention, electrical contacts 26a and 26b and electrical contacts 26c and 26d are generally aligned such that contacts 26a and 26c are electrically connected, such as by means of conventional plated-through holes or eyelets. Electrical contacts 26b and 26d are likewise electrically connected by means of conventional plated-through holes or eyelets. Electrical contacts 26a-26c and 26b-26d may each include an opening 20.

In alternate embodiments electrical contacts 26 may be provided with or without openings 20, and may comprise a conventional electrically conductive adhesive such as silver epoxy. The electrically conductive adhesive preferably has a relatively low-temperature cure to prevent damage to the components of sensor 10 during the adhesive curing process, and cures in a relatively short period of time so as to accommodate production of the sensor in quantity. The conductive adhesive facilitates electrical connection between sensor 10 and associated control circuitry, as will be described in further detail below.

Figure 1D:
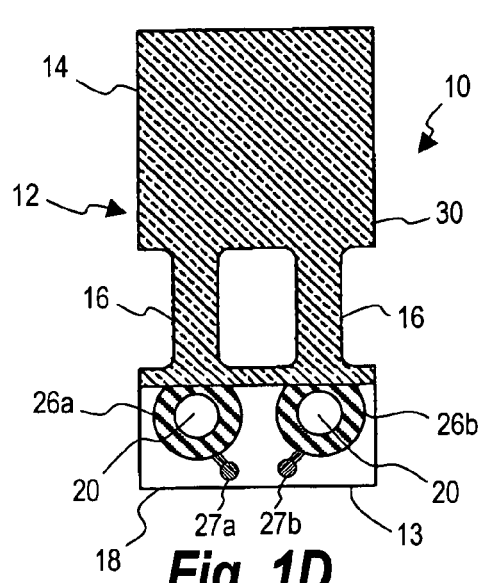
FIG. 1D is a top plan view of an air flow sensor according to an alternate embodiment of the present invention.
Figure 1E:
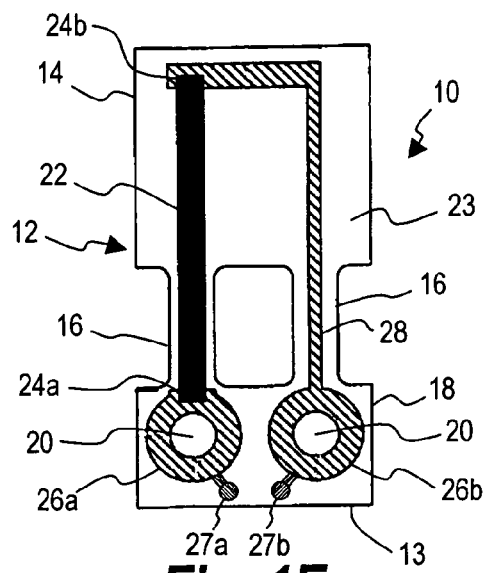
FIG. 1E is a top plan view of the air flow sensor of FIG. 1D with a protective covering removed to expose the components of the sensor.
Figure 1F:
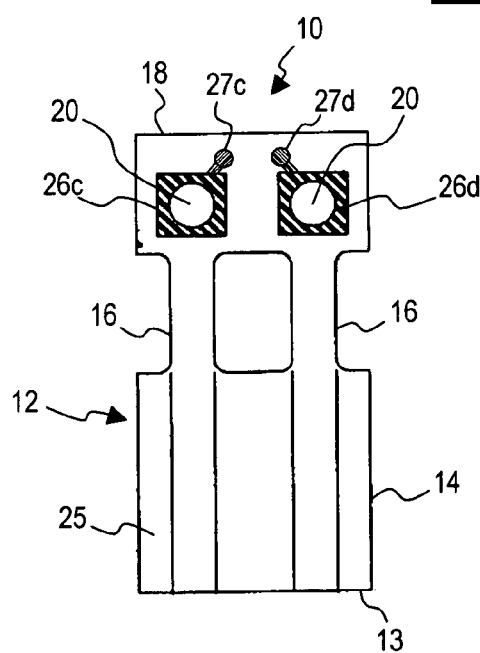
FIG. 1F is a bottom plan view of the air flow sensor of FIG. 1D.

In yet another alternate embodiment, electrical contacts 26a-26c and 26b-26d may be electrically connected by conventional printed wiring interconnection "vias." As shown in FIGS. 1D-1F, electrical contacts 26a-26c are electrically connected by vias 27a-27c. Likewise, electrical contacts 26b-26d are electrically connected by vias 27b-27d.

Figure 2A:
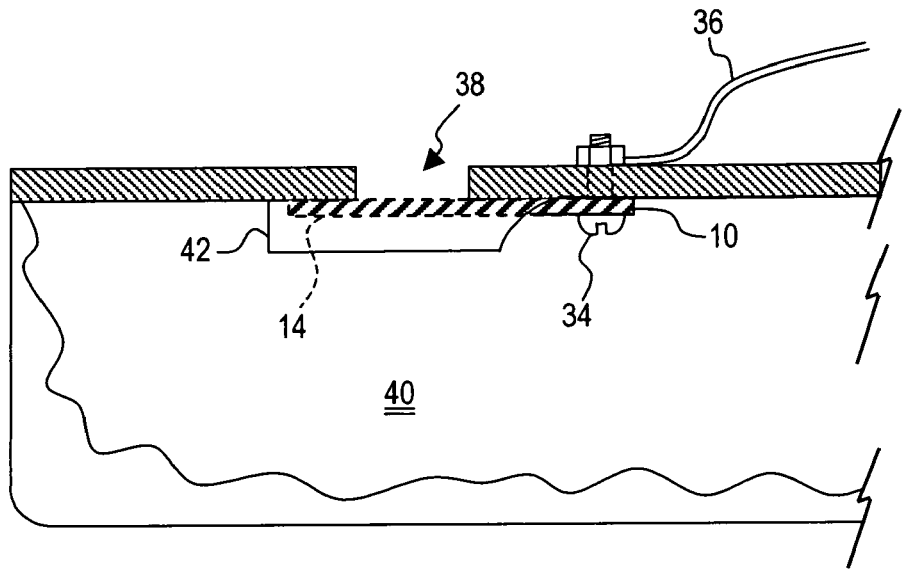
FIG. 2A is a side elevational view of an air flow sensor installed proximate an air inlet of an airway according to an embodiment of the present invention.
Figure 2B:
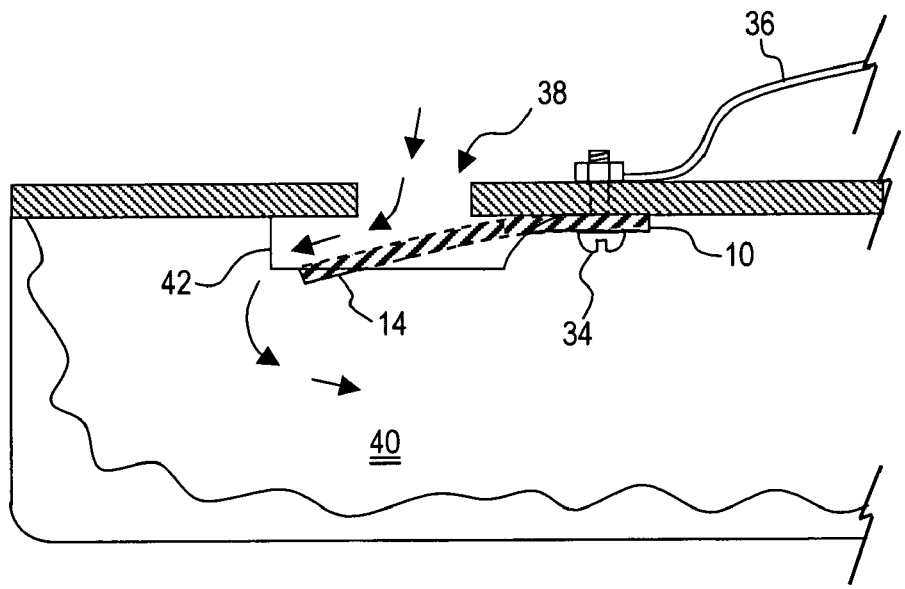
FIG. 2B is a side elevational view of the air flow sensor of FIG. 2A, showing the displacement of the sensor as a result of air flow.

Referring now to FIGS. 2A and 2B with continued reference to FIGS. 1A-1C, a sensor 10 adapted for use as an inhalation sensor is shown mounted in an airway 40 and proximate an air inlet 38. A filter or screen (not shown) may optionally be placed across air inlet 38 to prevent foreign matter from entering airway 40.

Sensor 10 is positioned in airway 40 such that inlet-covering portion 14 covers air inlet 38 at all times other than during inhalation, as shown in FIG. 2A. When the air pressure in airway 40 is lower than the ambient atmosphere around inlet 38, air flows through the inlet, causing sensor 10 to flex inwardly as shown in FIG. 2B. Flexure of sensor 10 causes flexure of transducer 22 (FIG. 1B), causing the transducer to change its electrical value. For example, if transducer 22 is a resistive element, flexure of sensor 10 may result in an increase or decrease in the resistance of the transducer.

An air shield 42 surrounds at least a portion of sensor 10 to direct air flowing into air inlet 38 such that the majority of the flowing air is directed at inlet-covering portion 14. The channeled air thus must displace sensor 10 to enter airway 40, enhancing movement of the sensor.

One or more electrical leads 36 are placed in electrical contact with contacts 26 of sensor 10. Electrical leads 36 may be a conventional flexible electronic printed circuit, or may be insulated electrical wires.

Openings in sensor 10, air shield 42, electrical leads 36 and airway 40 are aligned and secured together with at least one mounting means 34. Mounting means 34 may comprise any conventional fasteners, such as machine screws and nuts, rivets, self-tapping screws, studs, adhesives, sonic welding and molding. Further details regarding the mounting of sensor 10, air shield 42 and electrical leads 36 are provided below.

With further reference to FIGS. 2A and 2B, sensor 10 may function as a one-way air valve. As can be seen, sensor 10 deflects to allow air to flow into airway 40 via inlet 38 when the atmospheric pressure in the airway is less than the atmospheric pressure in the region of the air inlet. However, if the atmospheric pressure in airway 40 is greater than the atmospheric pressure in the region of air inlet 38, closing portion 14 of sensor 10 is forced against the air inlet, substantially preventing air from flowing from the airway to the air inlet. This feature is useful to prevent a patient from exhaling through a pulmonary medication delivery apparatus.

Figure 3:
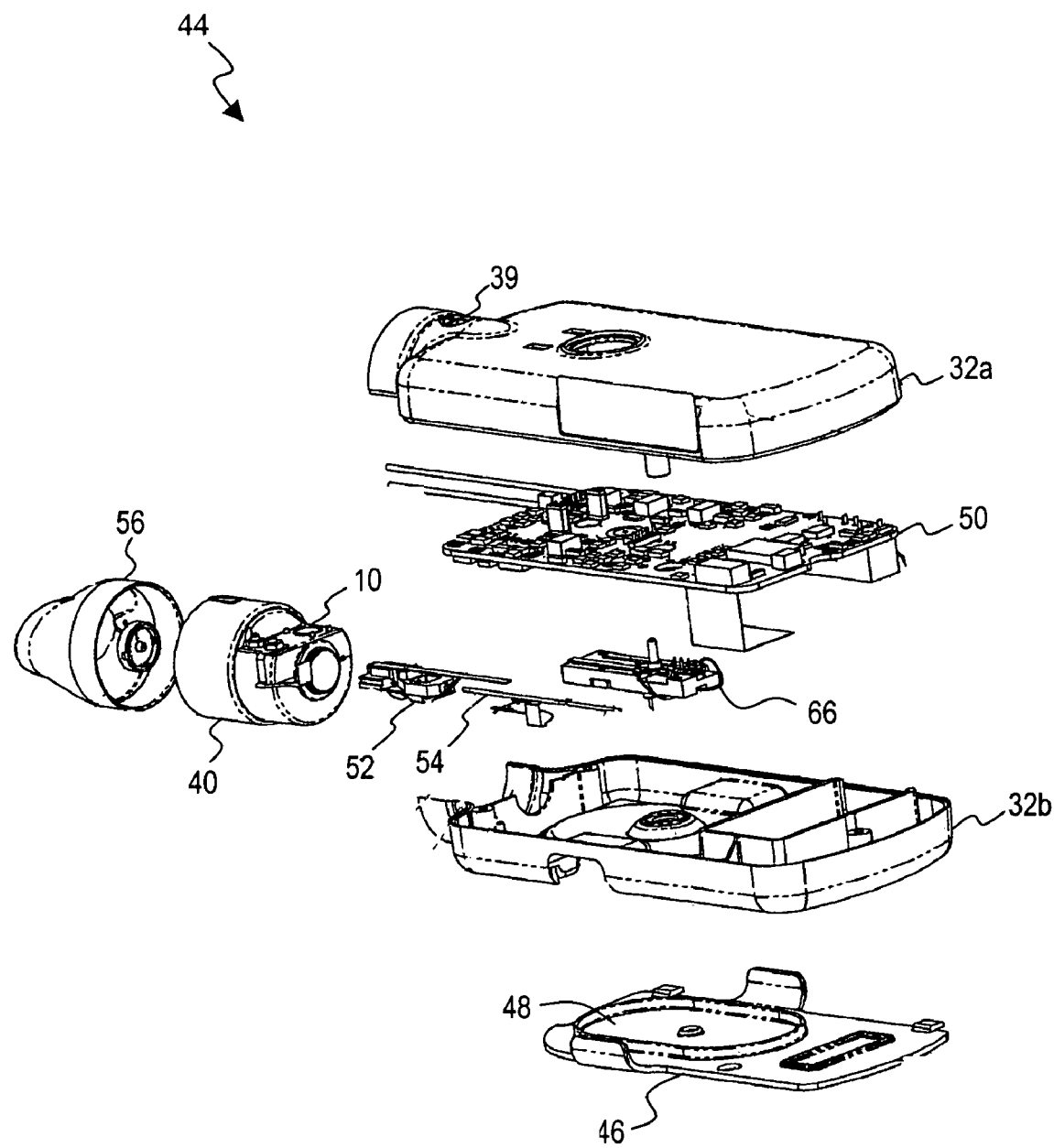
FIG. 3 is a perspective view of the general arrangement of a typical breath-actuated pulmonary medication delivery apparatus according to an embodiment of the present invention.

An example device that may utilize sensor 10 to advantage is an electrohydrodynamic ("EHD") pulmonary medication delivery apparatus ("PMDA"). The general arrangement of a typical EHD PMDA 44 is depicted in FIG. 3. It should be noted that EHD PMDA 44 is not intended to represent any particular embodiment of an EHD PMDA. In fact, sensor 10 may be used with numerous pulmonary medication delivery devices, such as the pulmonary aerosol delivery device disclosed by Zimlich, Jr., et al. in U.S. Pat. No. 6,397,838, incorporated herein by reference.

With continued reference to FIG. 3, EHD PMDA 44 comprises a controller portion 50 electrically coupled to a power supply, such as a battery (not shown). Controller portion 50 is also electrically coupled to a pump/valve 66. Pump/valve 66 is in turn mechanically coupled to a medication reservoir 48, position on a cover 46, for storing medication to be dispensed. A capillary tube 54 extends between pump/valve 66 and an aerosolation spray means 52. Aerosolation means 52 is pneumatically coupled to an airway 40. A mouthpiece 56 is mechanically coupled to airway 40. A housing 32, comprising an upper portion 32a and a lower portion 32b, encases the components of EHD PMDA 44. Upper housing portion 32a further comprises an opening 39, which is a source of air for air inlet 38 (not shown) of airway 40. Further details of the components and operation of EHD PMDA 44 are provided below.

Figure 4A:
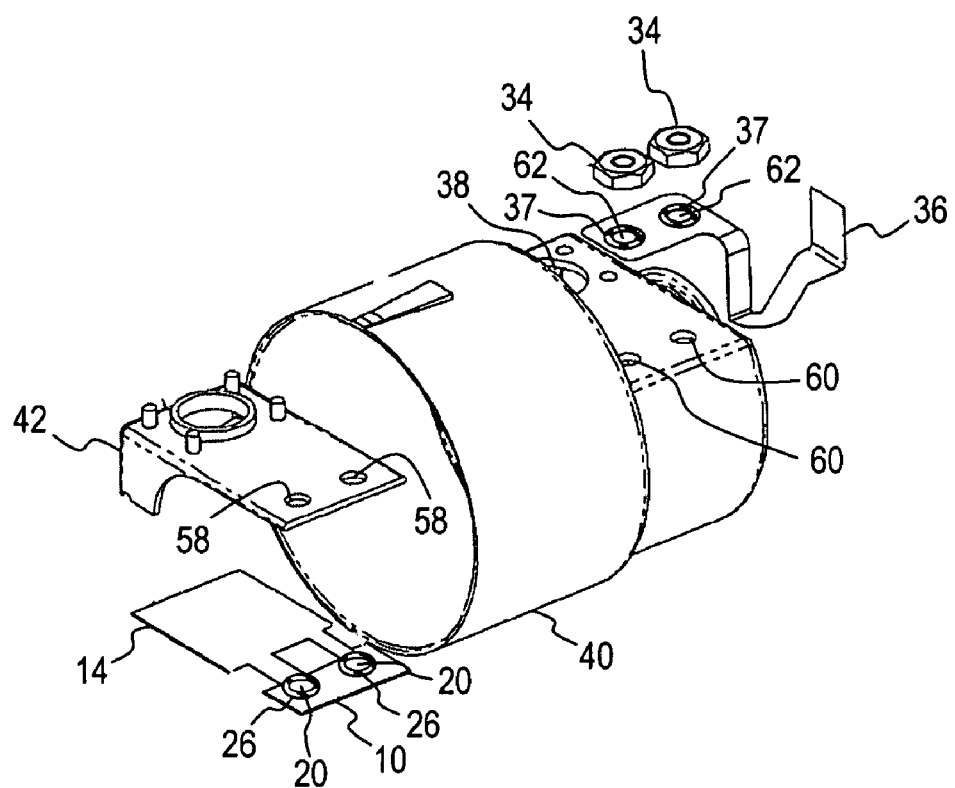
FIG. 4A is an expanded, exploded perspective view of an air flow sensor and an airway of the medication delivery apparatus of FIG. 3, according to an embodiment of the present invention.

FIG. 4A illustrates an expanded, exploded view of the airway 40 and sensor 10 of FIG. 3. Sensor 10 fits into an air shield 42, and both are located within airway 40 such that mounting means 34 may be installed through aligned openings 20 of the sensor, openings 58 of the air shield, openings 60 of the airway, and openings 62 of electrical leads 36. Inlet-closing portion 14 of sensor 10 acts as a closure for air inlet 38. Electrical leads 36 are located such that electrical contacts 37 of the electrical leads are placed into electrical communication with mounting means 34, which in turn is in electrical communication with contacts 26 of sensor 10. Thus, the sensor attachment points (i.e., openings 20) may be co-located with electrical contacts 26 such that mounting means 34 mechanically secures sensor 10 to airway 40 and also electrically couples the sensor to control portion 50 (see FIG. 3) via electrical leads 36. In an alternate embodiment of the present invention, a conventional conductive adhesive (not shown) may be used to electrically couple electrical contacts 26 of sensor 10 to electrical leads 36. Details of the use of conductive adhesive to form electrical connections are well-known and are left to the artisan.

Figure 4B:
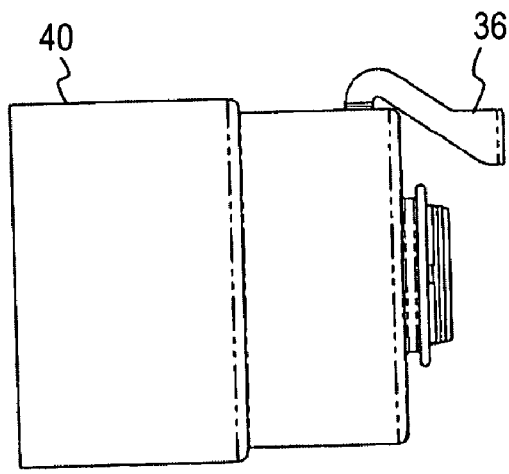
FIG. 4B is a side elevational view of the airway of FIG. 4A.

FIG. 4B is a side elevational view of the assembly of FIG. 4A, showing the components of FIG. 4A in an assembled condition.

Figure 5:
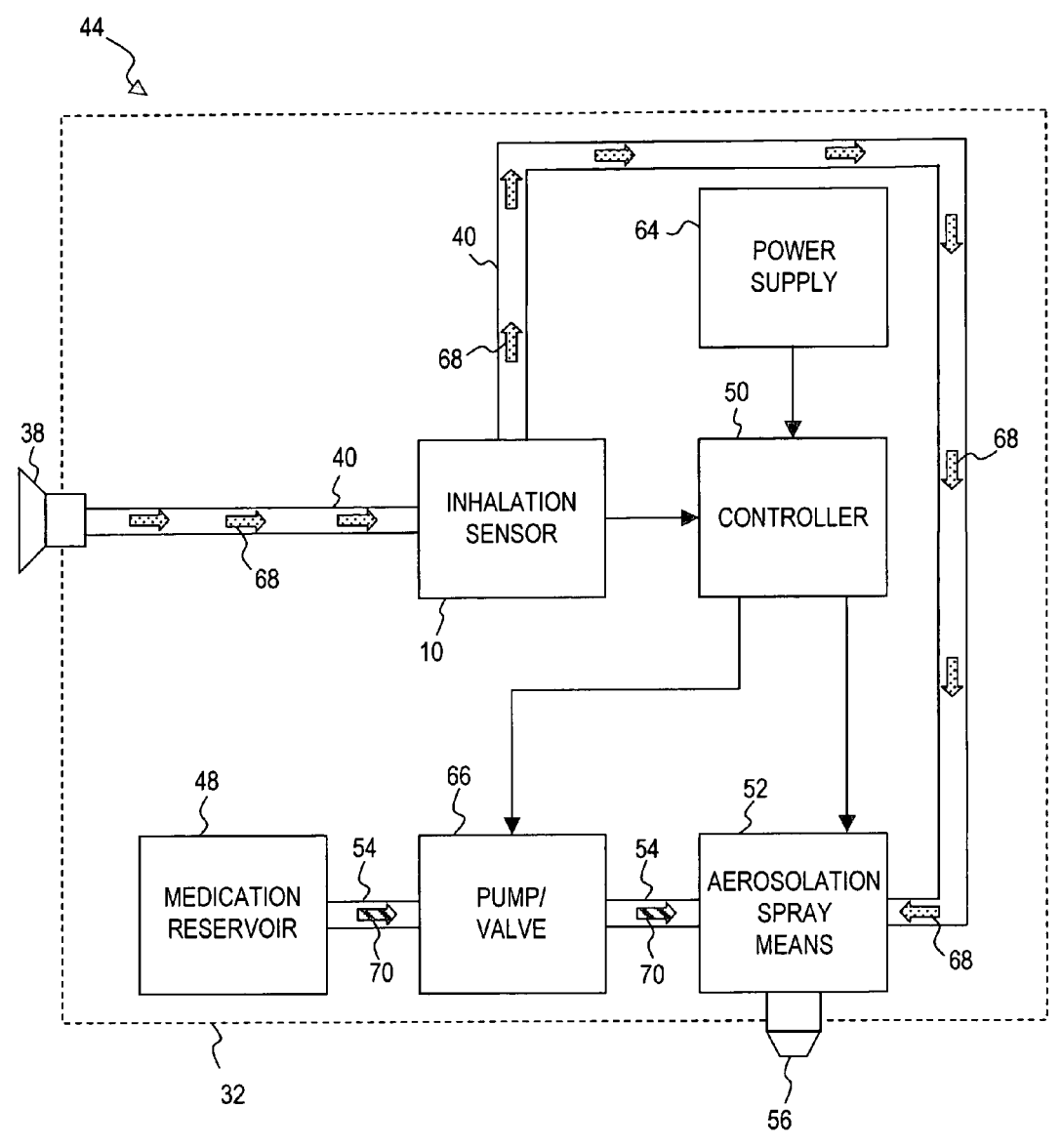

A functional block diagram of the EHD PMDA 44 of FIG. 3 is depicted in FIG. 5. Inhalation sensor 10, located proximate air inlet 38, is adapted to deflect as a result of air (identified as 68 in FIG. 5) moving through the air inlet and airway 40 due to the patient's inhalation via mouthpiece 56. When sensor 10 deflects in response to inhalation, the electrical value of transducer 22 (see FIG. 1B) changes, such as an increase in resistance.

Controller portion 50 is electrically powered by power supply 64 and monitors inhalation sensor 10 for a predetermined change in electrical value. When the predetermined change is detected by controller portion 50, indicating that the patient is inhaling, the controller portion actuates pump/valve 66.

Pump/valve 66 is electrically connected to power supply 64 and controller portion 50. When electrically actuated by controller portion 50, pump/valve 66 opens a conventional fluid valve which allows fluid (identified as 70 in FIG. 5) to be communicated from reservoir 48 to aerosolation spray means 52 via capillary tube 54. Pump/valve 66 also includes a pneumatic pump to urge the medication to flow from reservoir 48 to aerosolation spray means 52. Pump/valve 66 acts as a positive displacement fluid control, preventing evaporation and/or leakage of the medication in the reservoir 48 when the medication is not being dispensed. Pump/valve 66 may also be adapted to function with controller portion 50 to deliver a metered dose of medicine in accordance with predetermined criteria, such as actuation time or quantity of medicine and aerosolation spray means 52.

Aerosolation spray means 52 receives the medicine 70 from reservoir 48 via capillary tube 54 and pump/valve 66, and converts the medicine to an aerosol. Aerosolation is preferably accomplished by electrohydrodynamic means such as illustrated by, but not limited to, U.S. Pat. No. 6,397,838. The aerosolized medicine is mixed with air 68 flowing from air inlet 38 and is communicated to mouthpiece 56 for inhalation by the patient. The aerosolized medicine and air may be mixed passively by forcing the air flow of airway 40 to pass through the aerosolized medicine. Alternatively, the aerosolized medicine and air flow may be actively mixed, such as with a fan (not shown).

Mouthpiece 56 is adapted to fit into a patient's mouth and is pneumatically coupled to air inlet 38 by airway 40. Mouthpiece 52 is also pneumatically coupled to aerosolation spray means 52. Thus, air flowing in airway 40 is mixed with an aerosolized medicine for delivery to the patient when the patient inhales from mouthpiece 52. In an alternate embodiment, mouthpiece 56 may optionally be adapted to fit over a patient's nose and mouth to facilitate both nasal and oral breathing. This embodiment may be particularly useful for treating children.

Referring now to FIGS. 1-5 in combination, in operation a patient places the medication delivery apparatus 44 such that mouthpiece 56 is positioned inside the patient's mouth. The patient then inhales normally through mouthpiece 56, breathable air 68 being provided to the mouthpiece via air inlet 38 and airway 40. Movement of air through air inlet 38 causes displacement of sensor 10, causing the electrical value of transducer 22 to change, such as an increase or decrease in resistance. Controller portion 50 monitors the electrical value of transducer 22. When the change in electrical value of transducer 22 reaches a predetermined value, controller portion 50 actuates pump/valve 66 and aerosolation spray means 52. Medication from reservoir 48 is urged to aerosolation spray means 52 and is converted to an aerosol 70. The aerosolized medication mixes with the air flowing through airway 40, the air-medication mixture being delivered to mouthpiece 56 for pulmonary inhalation by the patient.

In a first alternate embodiment of the present invention, controller portion 50 detects the degree of change in the electrical value of sensor 10 and proportionally actuates pump/valve 66 and aerosolation spray means 52. In this embodiment the amount of medicine delivered to the patient is a generally constant proportion of the air delivered to mouthpiece 56.

In a second alternate embodiment of the present invention controller portion 50 may be configured to deliver a predetermined dosage of medication to the patient. Similarly, controller portion 50 may be configured to limit the delivery of medication to a predetermined concentration level or delivery rate.

As illustrated above sensor 10 may be used to advantage in medical applications to sense inhalation. However, sensor 10 may be used to satisfy a wide variety of consumer and industrial needs. For example, sensor 10 may be utilized as a transducer for electrical circuitry adapted to detect incoming air flow, such as air flow used in combustion, baking and curing systems. Likewise, sensor 10 may be used as a transducer for electrical circuitry adapted to monitor exhausts of various equipment to ensure that the exhaust system is functioning properly.

Although the previous example embodiments have utilized sensor 10 to detect air movement, one skilled in the art will recognize that the sensor may also be used to detect the flow of various gases. Likewise, sensor 10, properly environmentally sealed, may be used to detect the flow of liquids. Lastly, sensor 10 may be affixed or attached to any movable body to detect a change in position. For example, sensor 10 may be hingedly attached between a housing and an access panel in a piece of equipment such that the sensor is deflected when the access panel is open. In this manner sensor 10 may be used in association with electrical circuitry to detect the open access panel and prevent operation of the equipment, thereby avoiding potential harm to the equipment and/or personnel.

As previously discussed, sensor 10 may be used to detect inhalation by strategically placing the sensor in an airway such that the pressure differential caused by inhalation through the airway displaces the sensor. One skilled in the art will recognize that sensor 10 may also be adapted to detect pressure, such as is present with exhalation. With reference again to FIGS. 2A and 2B for a general illustration, in such embodiments sensor 10 is placed in an airway 40 such that when the air pressure present at inlet 38 is higher than the air pressure in airway 40, air will flow through the inlet to the airway, displacing the sensor inwardly. One skilled in the art will further recognize that the sensor may likewise be used as a one-way air valve in the same manner as previously discussed for the use of sensor 10 as an inhalation sensor.

While this invention has been shown and described with respect to a detailed embodiment thereof, it will be understood by those skilled in the art that various changes in form and detail thereof may be made without departing from the scope of the claims of the invention.

What is claimed is:

1. A gas or liquid flow sensor, comprising:
   (i) a non-conductive flexible substrate;
   (ii) a flexible transducer formed on the substrate, wherein said transducer consisting of a resistive ink or resistive elastomer;
   (iii) at least one flexible lead connecting the substrate to a mounting portion of the sensor; and
   (iv) first and second electrical contacts in electrical communication with the transducer;
   wherein the substrate and the flexible lead are displaceable in the presence of a stream of moving gas or liquid causing flexure of the transducer and changing an electrical value of the transducer and wherein said sensor is disposed in a pulmonary medication delivery device.

2. The sensor according to claim 1 wherein a protective covering covers at least a portion of the flexible transducer.

3. The sensor according to claim 1 wherein said gas is air.

4. The sensor according to according to claim 1 wherein at least one of the first and second electrical contacts are affixed to the mounting portion.

5. The sensor according to according to claim 1 wherein the electrical value of the flexible transducer changes relative to the flexure of at least the flexible substrate.

6. The sensor according to according to claim 1 wherein the flexible substrate substantially returns to an original orientation when a bending force impinging the flexible substrate is removed.

7. The sensor according to according to claim 1 wherein the sensor forms at least a portion of a one-way valve in a stream of moving gas.

8. The sensor according to claim 1 wherein said resistive transducer is a resistive ink.

9. The sensor according to claim 8 wherein said resistive ink comprises conductive carbon particles in a binder.

10. The sensor according to claim 8 wherein said non-conductive flexible substrate is made of a material selected from the group consisting of a polyester, polyimide and a fluoropolymer.

11. The sensor according to according to claim 10 wherein said non-conductive flexible substrate is made of polyimide.

12. The sensor according to claim 1 wherein the flexible transducer includes a portion formed on the flexible lead.

13. The sensor according to claim 1 wherein the flexible substrate and the flexible lead are integral to one another.

14. The sensor according to claim 1 wherein the electrical value of the flexible transducer changes relative to the flexure of the flexible substrate and the flexible lead.

15. The sensor according to claim 1 wherein said pulmonary medication delivery device is an electrohydrodynamic aerosolization device.

16. The sensor according to claim 15 wherein said electrohydrodynamic aerosolization device is a hand-held device.

17. The sensor according to claim 1 wherein the first and second electrical contacts are affixed to the first side of the flexible substrate; wherein a third electrical contact and a fourth electrical contact are affixed to the second side of the flexible substrate; and wherein said third electrical contact is in electrical communication with said first electrical contact and said fourth electrical contact is in electrical communication with said second electrical contact.

18. The sensor according to claim 1 wherein the body of the sensor is generally rectangular, circular, triangular, elliptical, polygonal, trapezoidal, U-shaped, and parallelogram in shape.

19. The sensor according to claim 1 wherein the body of the sensor is generally rectangular in shape.

* * * * *